(12) United States Patent
de Troostembergh et al.

(10) Patent No.: US 6,177,064 B1
(45) Date of Patent: *Jan. 23, 2001

(54) ANTI-CARIOGENIC ACTIVITY OF ERYTHRITOL

(75) Inventors: Jean-Claude Marie-Pierre Ghislain de Troostembergh, Tielt-Winge; Jozef Frans Victor Goossens, Bierbeek, both of (BE)

(73) Assignee: Cerestar Holding B.V., La Sas Van Gent (NL)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/844,452

(22) Filed: Apr. 18, 1997

(30) Foreign Application Priority Data

Apr. 19, 1996 (GB) .................................. 96081534

(51) Int. Cl.[7] .................. A61K 7/16; A23G 1/08; A23G 3/30; C08B 36/18
(52) U.S. Cl. .............. 424/49; 424/48; 424/440; 426/3; 426/5; 426/98; 426/99; 426/103; 426/548; 426/572; 426/658; 426/660; 426/804
(58) Field of Search .............. 424/48, 49, 440; 426/35, 98, 99, 103, 548, 572, 658, 668, 804

(56) References Cited

U.S. PATENT DOCUMENTS

| | | | |
|---|---|---|---|
| 3,876,794 | * 4/1975 | Rennhard | 426/152 |
| 3,943,241 | * 3/1976 | Anderson et al. | 424/54 |
| 4,518,581 | * 5/1985 | Miyake et al. | 424/48 |
| 4,726,943 | * 2/1988 | Klueppel et al. | 424/54 |
| 4,883,685 | * 11/1989 | Kondou | 426/658 |
| 4,886,677 | * 12/1989 | Kondou | 426/658 |
| 5,043,169 | * 8/1991 | Cherukuri et al. | 426/5 |
| 5,064,672 | * 11/1991 | Mazur | 426/531 |
| 5,126,160 | * 6/1992 | Giddey et al. | 426/564 |
| 5,244,690 | * 9/1993 | Van der Schueren et al. | 426/660 |
| 5,314,701 | * 5/1994 | Mentink et al. | 426/103 |
| 5,378,481 | * 1/1995 | Minamikawa et al. | 426/99 |
| 5,397,579 | * 3/1995 | Yatka et al. | 426/3 |
| 5,425,957 | * 6/1995 | Gaim-Marsoner et al. | 426/98 |
| 5,436,329 | * 7/1995 | Caboche | 536/103 |
| 5,462,760 | * 10/1995 | Serpelloni et al. | 426/572 |
| 5,468,509 | * 11/1995 | Schlup et al. | 426/548 |
| 5,494,685 | * 2/1996 | Tryrpin et al. | 426/658 |
| 5,567,467 | * 10/1996 | Kondou | 426/659 |
| 5,603,970 | * 2/1997 | Tyrpin et al. | 426/5 |
| 5,629,042 | * 5/1997 | Serpelloni et al. | 426/600 |
| 5,637,334 | * 6/1997 | Yatka et al. | 426/3 |
| 5,651,936 | * 7/1997 | Reed et al. | 426/5 |
| 5,659,028 | * 8/1997 | Coussement et al. | 536/123 |
| 5,667,573 | * 9/1997 | Kondou | 106/194.2 |
| 5,711,982 | * 1/1998 | Takemori et al. | 426/580 |

FOREIGN PATENT DOCUMENTS

| | | | |
|---|---|---|---|
| 9325 | * | 4/1980 | (EP) . |
| 303295A2 | * | of 1989 | (EP) . |
| 0 512 910 A2 | | 11/1992 | (EP) . |
| 676147A1 | * | 10/1995 | (EP) . |
| 2654308A1 | * | of 1991 | (FR) . |
| 2705207A1 | * | of 1994 | (FR) . |
| 2706737A1 | * | of 1994 | (FR) . |
| 63-258557 | * | 10/1988 | (JP) . |
| 01051045A2 | * | 2/1989 | (JP) . |
| 01312960A2 | * | 2/1989 | (JP) . |
| 01095741A | * | 4/1989 | (JP) . |
| 01098457A | * | 4/1989 | (JP) . |
| 01148173A | * | 6/1989 | (JP) . |
| 01171455A | * | 7/1989 | (JP) . |
| 01225458A | * | 9/1989 | (JP) . |
| 01265852A | * | 10/1989 | (JP) . |
| 02104243A2 | * | 4/1990 | (JP) . |
| 05030913A2 | * | 2/1993 | (JP) . |
| 05137518A | * | 6/1993 | (JP) . |
| 05137518A2 | * | 6/1993 | (JP) . |
| 05137535A2 | * | 6/1993 | (JP) . |
| 07123923A2 | * | 5/1995 | (JP) . |
| 07274837A | * | 10/1995 | (JP) . |

OTHER PUBLICATIONS

Kawanabe et al Caries Research 26(5): 358–362, 1992.*
Ropper et al Starch 45(11): 400–405, 1993.*
Goossens et al Adv. Sweeteners :150–186, 1996.*
Shinsato Cereals Foods World 41(5): 372–375, 1996.*
Tatluck Food Technology Europe 2(1) : 30 32 34, 1995.*
Caries Research, vol. 26, 1992, Basel, pp. 358–362, Kawanabe et al "Noncariogenicity of Erythritol as a substrate".
Food Trade Review, vol. 64, No. 2, Feb. 1994, Bromley, Kent, p. 75 "New Horizons in Low Calorie Bulk Sweetteners".

* cited by examiner

Primary Examiner—Shep K. Rose
(74) Attorney, Agent, or Firm—Pillsbury Madison & Sutro LLP

(57) ABSTRACT

The present invention anti-cariogenic activity of erythritol. The invention further discloses the use of erythritol in food preparations as an at least partial replacer of sugar or other cariogenic sweetening agent. Erythritol is used in combination with normally employed sweetening agents and the favourable characteristics of the erythritol are preserved while the amount of erythritol used is much less than what would be needed to replace the sugar completely.

5 Claims, 12 Drawing Sheets

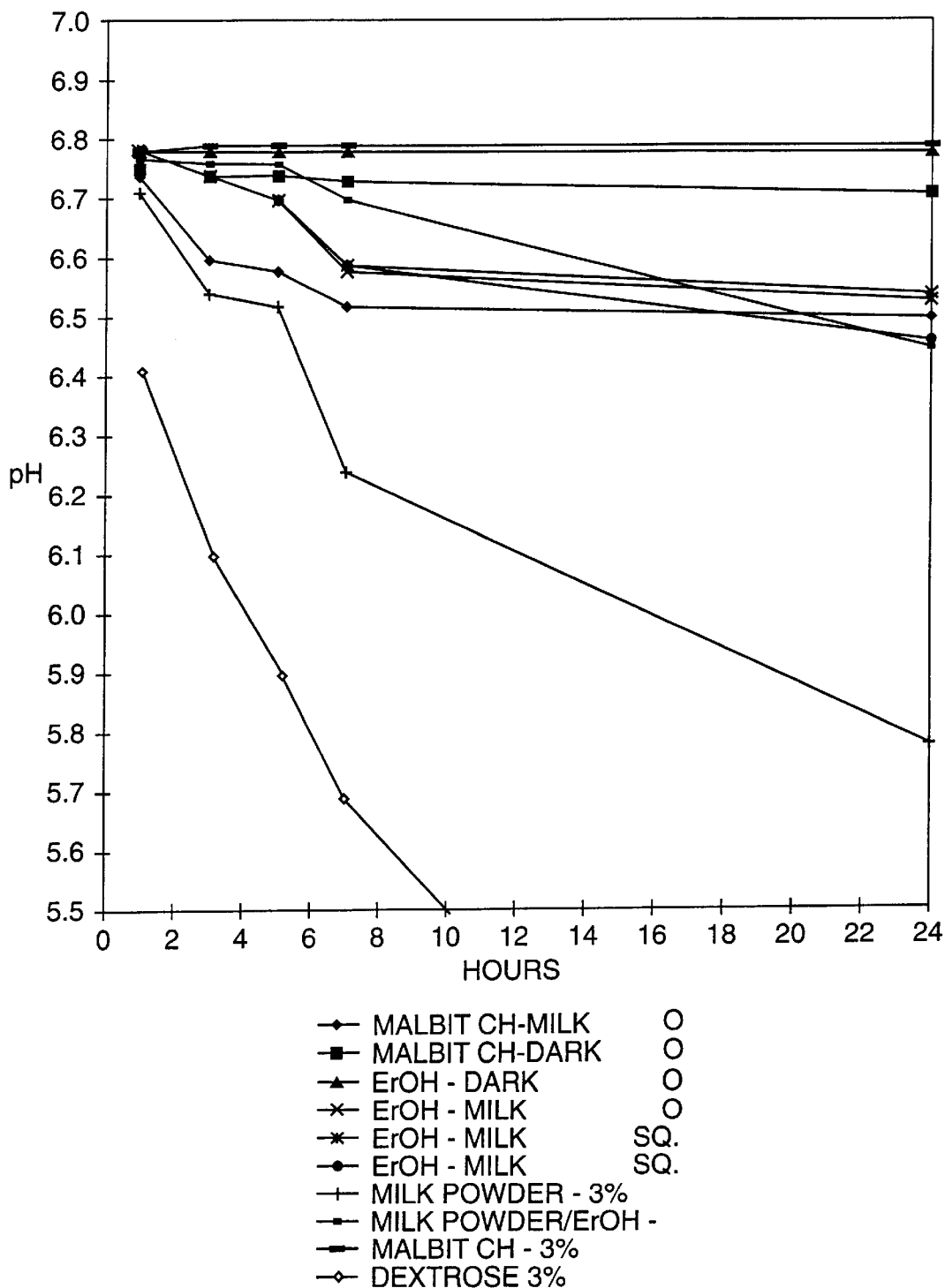

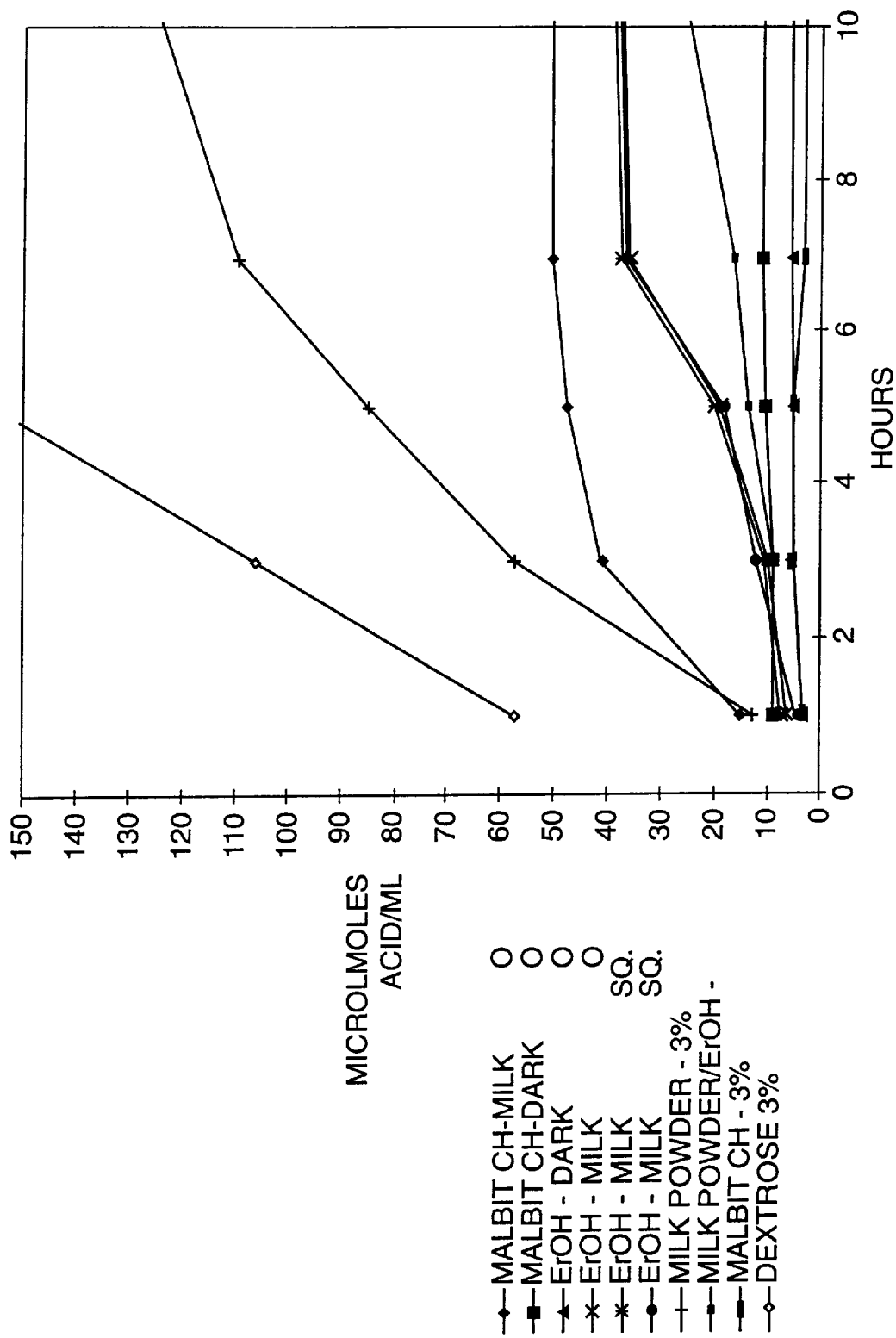

ANTI-CARIOGENIC ACTIVITY OF ERYTHRITOL

TECHNICAL FIELD

The present invention discloses the anti-cariogenic activity of erythritol. The invention further discloses the use of erythritol in food preparations as an at least partial replacer of sugar or other cariogenic sweetening agents. Erythritol is used in combination with normally employed sweetening agents and the favourable characteristics of the erythritol are preserved. The usefulness of this anti-cariogenic effect is demonstrated in food preparations such as chewing gum, chocolate and candies wherein a part of the sugar, lactose, sorbitol or maltitol is replaced with erythritol.

BACKGROUND OF THE INVENTION

Polyhydric alcohols are used in food compositions to retain the original quality of the food on ageing and shipping or to obtain a texture or product quality that was not present in the original product. Sorbitol, glycerol, mannitol and other polyols are already used on a large scale as food additives.

Erythritol, a naturally occurring polyol sweetener, has relatively recently become available in significant amounts. Erythritol is used for its capacity to replace sugar while preserving the sweet taste. Erythritol is 60% as sweet as sucrose at the normal use level and is sweeter than mannitol and sorbitol. It is also used because it is excreted unmetabolised and therefore leads to an important calorie reduction.

Apart from the calorie reduction erythritol can also provide the texture of a 'fatty mouthfeel'. Because of this characteristic erythritol is also suitably used as a fat replacer.

Since erythritol is not metabolised it will have little or no effect upon the normal body function. It may therefore be used in foodstuffs designed for people whose metabolizable carbohydrate intake must be restricted due to diabetes or obesity.

Erythritol is also used in sugarless chewing-gum applications. It is known that erythritol is not fermented by bacteria appearing in the mouth flora, and especially by Streptococci, therefore erythritol does not give rise to acidification. This acidification is one of the causing agents of caries. The Streptococci are also responsible for the formation of water-insoluble glucan which in turn forms the dental plaque. The dental plaque will retain microorganisms and therefore also stimulates caries formation. Products which contain erythritol instead of other sweetening agents have been tested in the so-called Mühlemann test (Imfeld, Th. and Mühlemann, H. R. J, Prev. Dentistry 4 8–14 (1977) and Imfeldt, Th. and Duhamel, L. Revue d'Odonto-stomatologie 9: 27–38 (1980)). This test is based on the intra-oral measurement of plaque pH. In this test a criterium for the indication 'safe for teeth' is developed. A product or composition is called 'safe for teeth' if the pH in the mouth does not drop below 6 after consumption of the product or composition. According to this criterium erythritol is considered as 'safe for teeth'. Replacement of sugar by erythritol therefore reduces the amount of caries to a considerable degree.

All this is known for some time as evidenced by the vast amount of literature covering an ever growing field of potential applications for polyols in general and for erythritol in particular.

Erythritol is commercially produced by fermentation of glucose. Potential fermentation processes are described in European patents EP 0 136 802, EP 0 136 803, EP 0 136 804, EP 0 136 805, EP 0 262 463, EP 0 327 016 and EP 0 327 342. Chemical methods for the production of erythritol are well known and include hydrogenolysis of dialdehyde starch, reduction of formaldehyde and hydrogenolysis of sorbitol.

Erythritol, which is extensively marketed in Japan, is increasingly used as a sugar replacer in such applications as chocolates, candies, pie fillings, soft drinks etc. European patent application EP 0 009 325 describes the use of erythritol in the form of a sugarless cariostatic composition comprising at least 5% erythritol. The preferred use of this composition is in toothpaste or chewing gum and it is reported that preferably the sugars are completely replaced with erythritol. Moreover all examples relate to the total replacement of sugar.

European patent EP 0 511 761 describes instant pie fillings containing erythritol and sorbitol.

European patent EP 0 530 995 describes the application of erythritol or maltitol for the preparation of low cariogenic and low calorie lozenges.

European patent application EP 0 727 146, which was not pre-published, discloses a chocolate composition containing erythritol and an amount of maltitol sufficient to mask the cooling effect of erythritol. The chocolate preparations contain no sugar and the application only describes bitter (black) chocolate i.e. chocolate containing no milk powder or lactose.

Among the references relating to the non-cariogenic effect of erythritol the following are specifically pointed out. Kawanabe et al. Caries Res. 26 358–362 (1992) describes the non-cariogenecity of erythritol as a substrate. After studies in which rats were fed diets containing erythritol, sucrose or starch it was concluded that erythritol was not utilized as a substrate for tooth plaque formation. Furthermore, Streptococci did not produce lactic acid.

European patent application EP 0 561 089 describes the use of different combinations of hydrogenated monosaccharides with polysaccharides. No specific mention is made of any special effects observed with erythritol let alone an anti-cariogenic effect of erythritol. Furthermore erythritol is not used in any of the experiments.

U.S. Pat. No. 4,518,581 describes the low- or anti-cariogenic properties of isomalto-oligosaccarides. In Table 1 it is demonstrated that erythritol, in an amount of 10% with respect to sucrose, does not inhibit the water-insoluble glucan formation by Streptococcus mutans 6715. Erythritol is therefore not classified as anti-cariogenic according to the criteria developed in this U.S. patent.

One of the major drawbacks of the use of erythritol as a sugar replacer is that it is much more expensive than some of the substances which it replaces. It would therefore be interesting to replace only a part of the sugar by erythritol while at the same time preserving the characteristics of erythritol specifically its non-cariogenic effect.

SUMMARY OF THE INVENTION

The present invention discloses that erythritol has an anti-cariogenic effect.

The present invention further discloses the use of erythritol as a partial replacer of sugar or of other cariogenic sweetening agents. Specifically, the invention discloses the use of erythritol as an anti-cariogenic agent in the preparation of food products, tooth paste and mouth rinse. The invention further disloses the use of erythritol as a sugar replacer in chocolate, specifically in milk chocolate.

The invention further discloses a sugar free non-cariogenic milk chocolate.

Erythritol is used for partial replacement of sugar in different applications and it is demonstrated that the product can still be considered as non-cariogenic.

The present invention further discloses the use of a non-cariogenic combination of erythritol and other sweetening agents such as glucose, lactose, sorbitol, xylitol, maltitol and lactitol.

BRIEF DESCRIPTION OF THE FIGURES

FIG. 11 shows the pH development when S. mutans is incubated with milk and dark chocolate containing erythritol.

FIG. 12 shows the total amount of acid produced upon incubation of S. mutans with milk and dark chocolate containing erythritol.

DETAILED DESCRIPTION OF THE INVENTION

Figure 1:
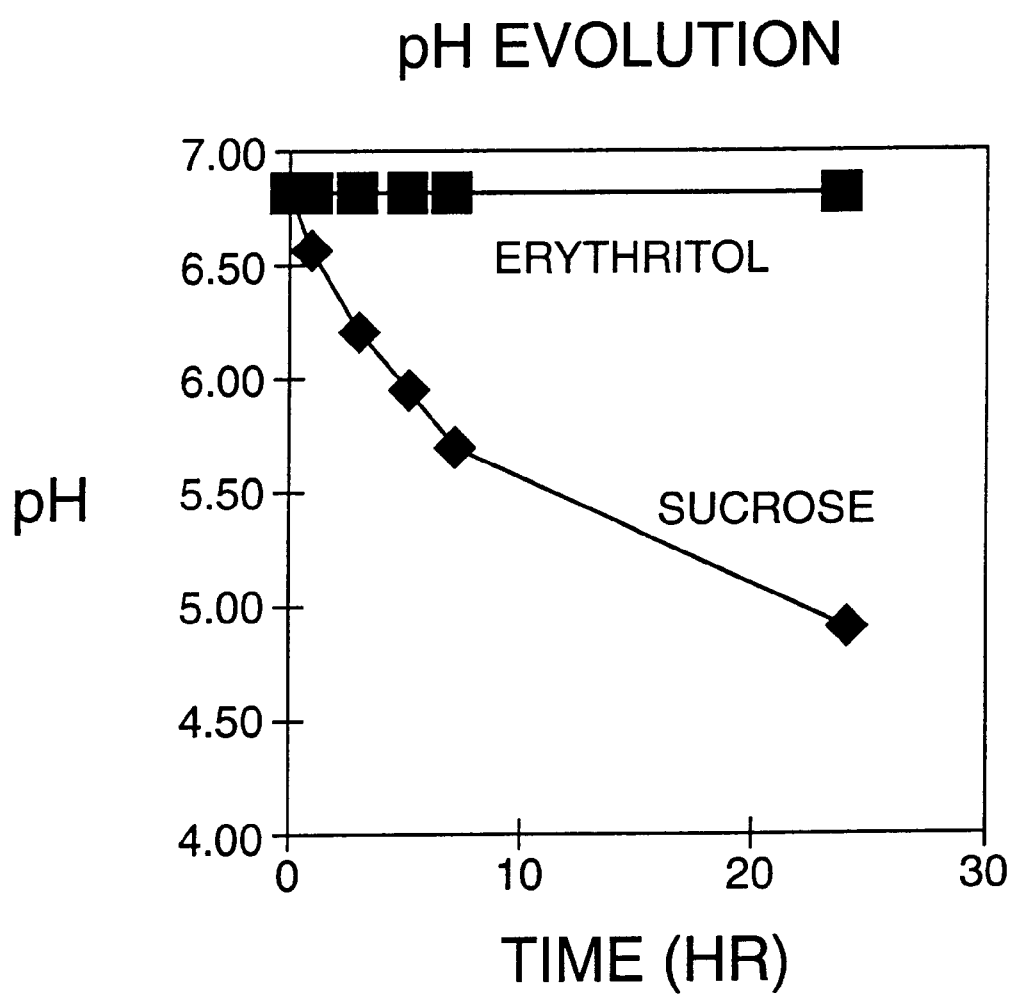
FIG. 1 shows the pH development when S. mutans in the in-vitro test medium is incubated with erythritol and with sucrose.

The present invention discloses that erythritol has an anti-cariogenic effect. For the purpose of the present invention by anti-cariogenic effect is meant that a composition which contains a sweetening agent which is cariogenic becomes non-cariogenic by the addition of erythritol. This effect is shown by in-vitro acid production tests. It is assumed that if the pH of a S. mutans culture does not drop below a certain pH level when an erythritol containing composition is added the composition is non-cariogenic and can be called 'safe for teeth' according to the criteria developed by Mühlemann. Replacing a part of the normally present cariogenic sweetening agent with erythritol gives a product which does not give rise to excessive acid production in spite of the presence of the normally cariogenic sweetening agent. The present invention also discloses foodstuff, mouth rinse and tooth paste compositions wherein a part of the sweetener has been replaced with erythritol.

Whereas in general the non-cariogenicity of erythritol has been reported by testing pure erythritol solutions or sugarless compositions or products containing erythritol as a sugar replacer the present inventors have surprisingly found that addition of an amount of erythritol to a composition or product containing a sugar still results in a non-cariogenic product. It is thus disclosed that erythritol has an anti-cariogenic effect.

The present invention describes the use of erythritol as an anti-cariogenic agent in food preparations, tooth paste and mouth rinse.

Erythritol is used in a composition containing a normal sweetener wherein a part of this sweetener is replaced with erythritol characterised in that the composition is non-cariogenic. The amount of erythritol required to achieve this depends on the amount and the type of the other (cariogenic) sugar which is present. In milk chocolate preparations the sugar is replaced with erythritol which can counteracts the presence of lactose which is of course essential and is not replaced.

Positive results have been found when erythritol was present in an amount as low as between 10 and 20% (w/w) of the sugar component. It is evident that the mentioned anti-cariogenic activity will than also be present when higher amounts of erythritol are used.

Although the effect is mentioned for replacement of sucrose it is also possible to replace a part of the sweetening agent which is a polyol itself. As shown hereinafter sorbitol and lactitol show an important acid production which is not found when these polyols are partly replaced with erythritol. Moreover the effect of erythritol is also to protect against acidifying sugars after the erythritol composition is already swallowed.

The present invention is thus illustrated in compositions which further comprised as the normal sweetener sucrose, sorbitol, lactitol, maltitol and isomalt. In a further application it is shown that the cariogenic effect of lactose which is present in milk powder is counteracted by the presence of erythritol. It is shown for the first time how non-cariogenic sugar free milk chocolate is obtained.

Food compositions in which the mixtures can be applied are all foods wherein normally a sugar component or other sweetening agent is used. It is further possible to use these mixtures in non-food compositions such as tooth paste, mouth rinse or chewing gum.

Specific compositions are given in the examples and illustrate the combined use of erythritol and other sweetening composition in gelatine gums, gum arabic pastilles, chewy candies, hard candies, fondant and fudge. The examples further show the use in partial replacement of sorbitol in chewing gum. Other interesting applications are in chocolate.

In order to illustrate the above described anti-cariogenic activity the following experiments were performed.

In-vitro incubation of S. mutans with erythritol and with sucrose as a control and measurement of the pH development in the solution showed that erythritol does not give rise to a change in pH (FIG. 1). Erythritol can therefore be classified as non-cariogenic in this in-vitro test system.

Figure 2:
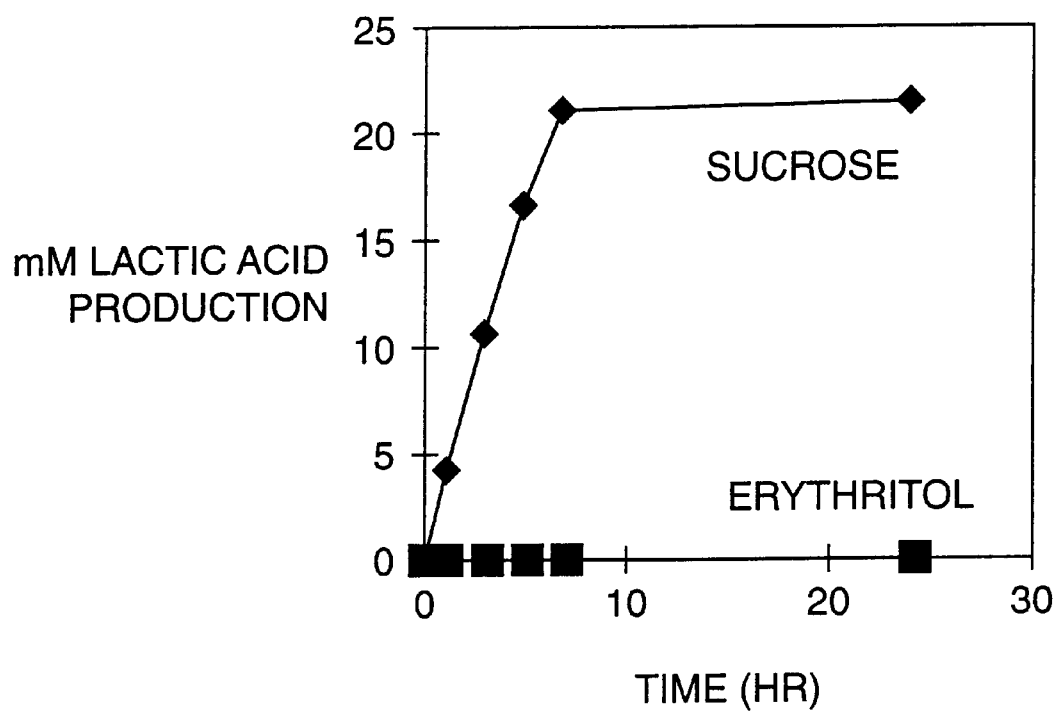
FIG. 2 shows the lactic acid production when S. mutans in the in-vitro test medium is incubated with erythritol and with sucrose.

In the same experiment the lactic acid production was measured and it was found that erythritol did not give rise to lactic acid production (FIG. 2).

Figure 3:
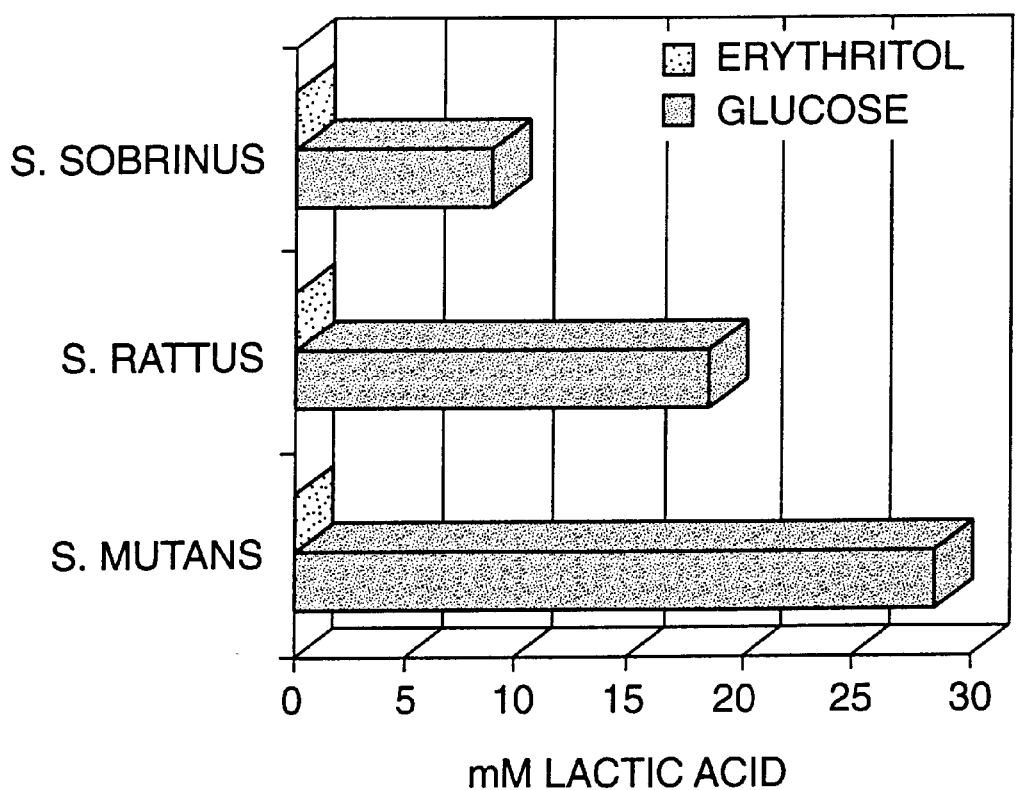
FIG. 3 shows the lactic acid production when different Streptococcus strains are incubated with erythritol or glucose.

In order to confirm whether this phenomenon was specific for the S. mutans species different Streptococci were evaluated. It was found that also S. sobrinus and S. rattus did not produce acid upon incubation with erythritol (FIG. 3).

Figure 4:
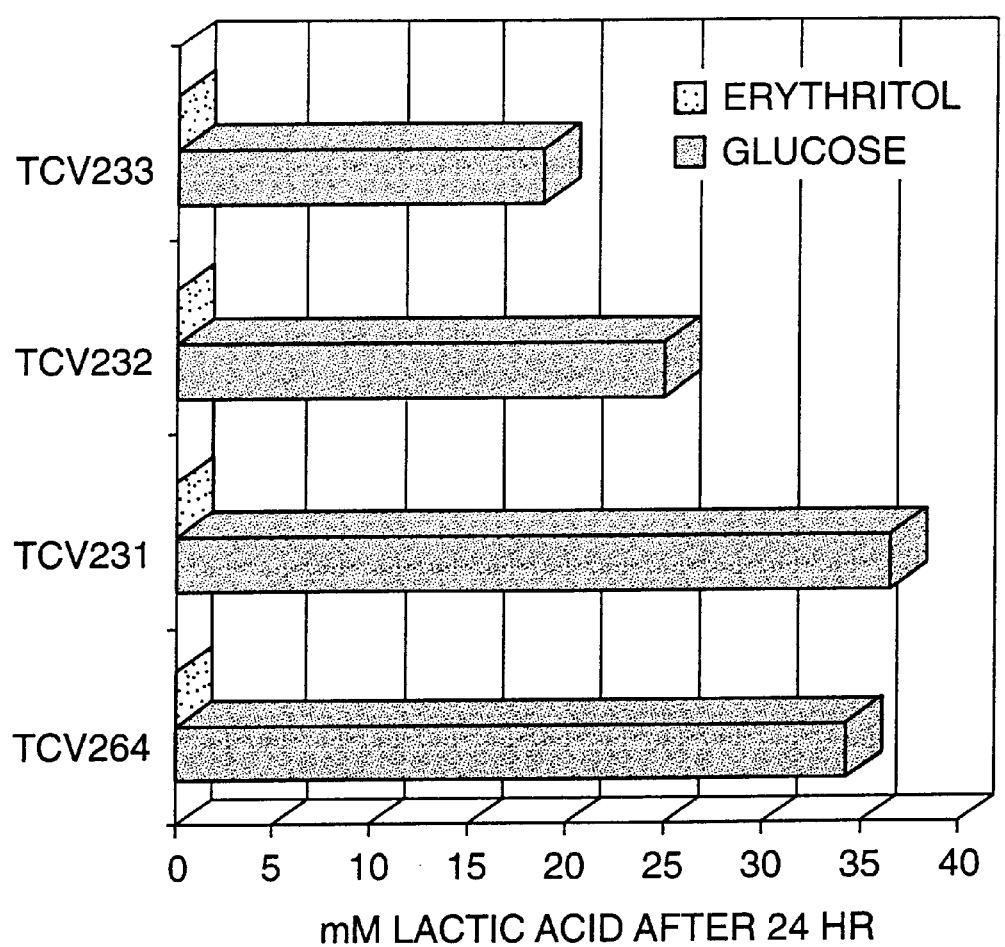
FIG. 4 shows the lactic acid production when different S. mutans strains are incubated with erythritol or glucose.

The lactic acid production when different *S. mutans* strains were incubated with erythritol was also absent (FIG. 4).

It can therefore be concluded that erythritol has a non-cariogenic activity when different strains and species of Streptococcus are used.

Figure 5:
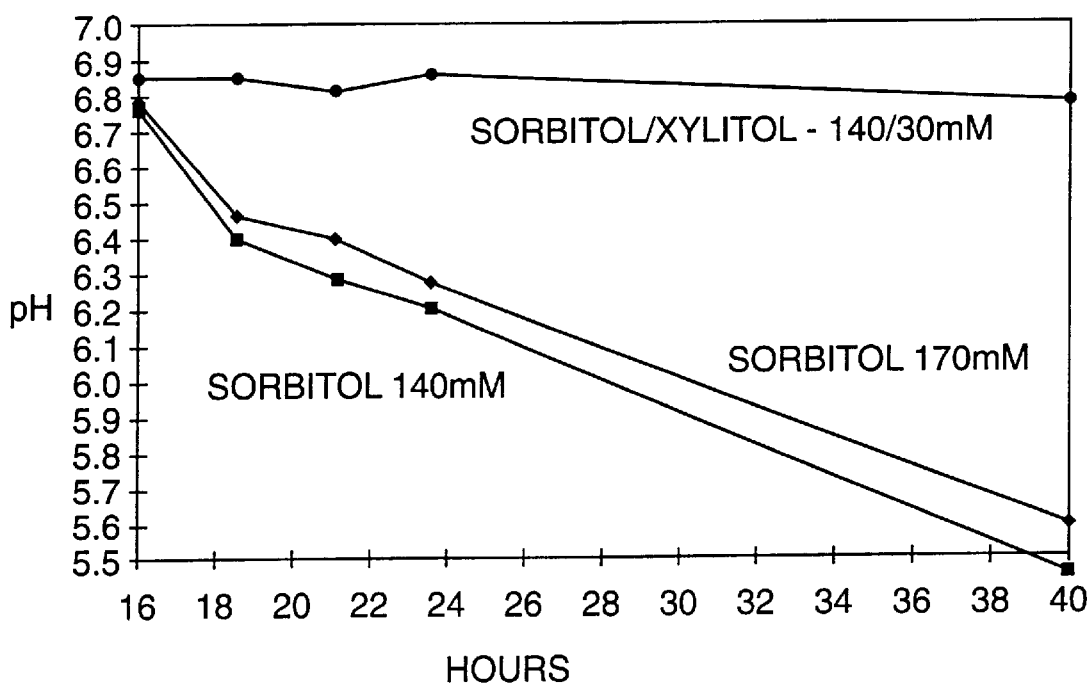
FIG. 5 shows the anti-cariogenic effect of xylitol in combination with sorbitol.
Figure 6:
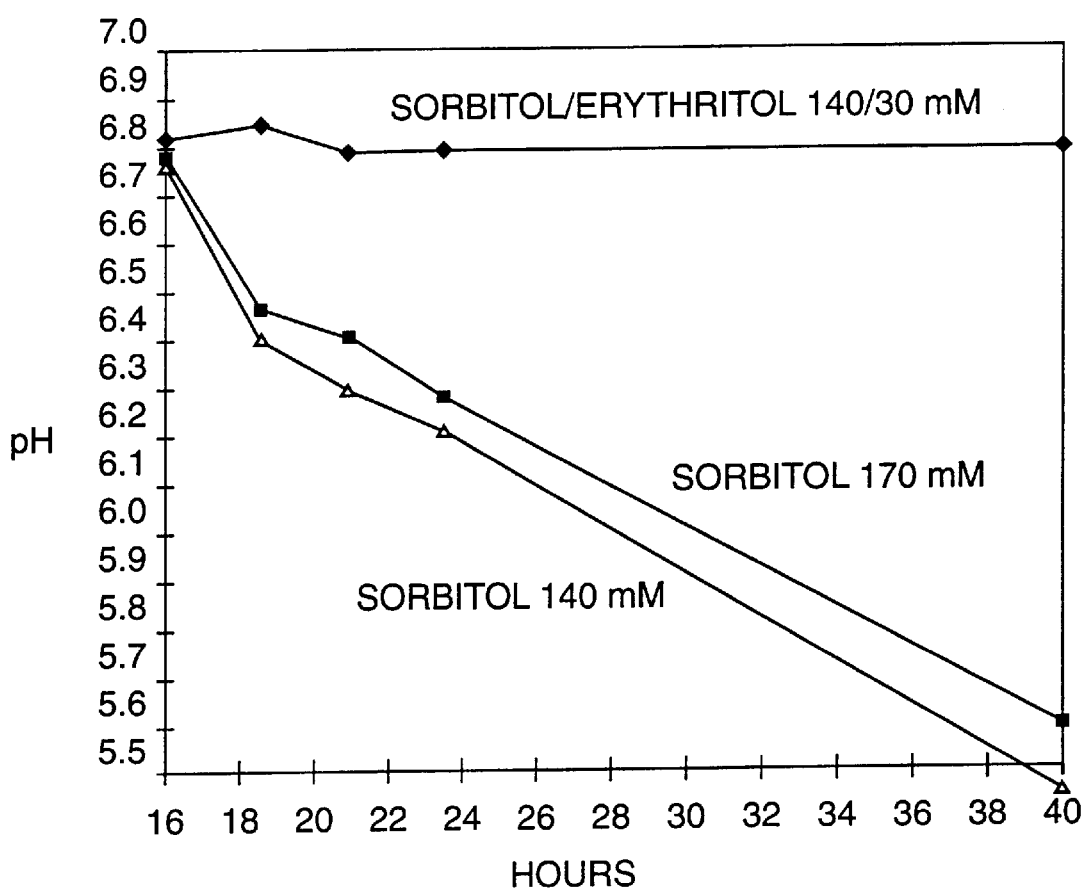
FIG. 6 shows the anti-cariogenic effect of erythritol in combination with sorbitol.

The anti-cariogenic activity of erythritol was shown by incubation of sorbitol together with erythritol. The use of a final concentration 140 mM of sorbitol did not give rise to acid production in the presence of 30 mM erythritol. The same experiment performed using xylitol instead of erythritol showed that the anti-cariogenic activity of erythritol appears to be similar to that of xylitol (FIGS. 6 and 5 respectively).

Figure 7:
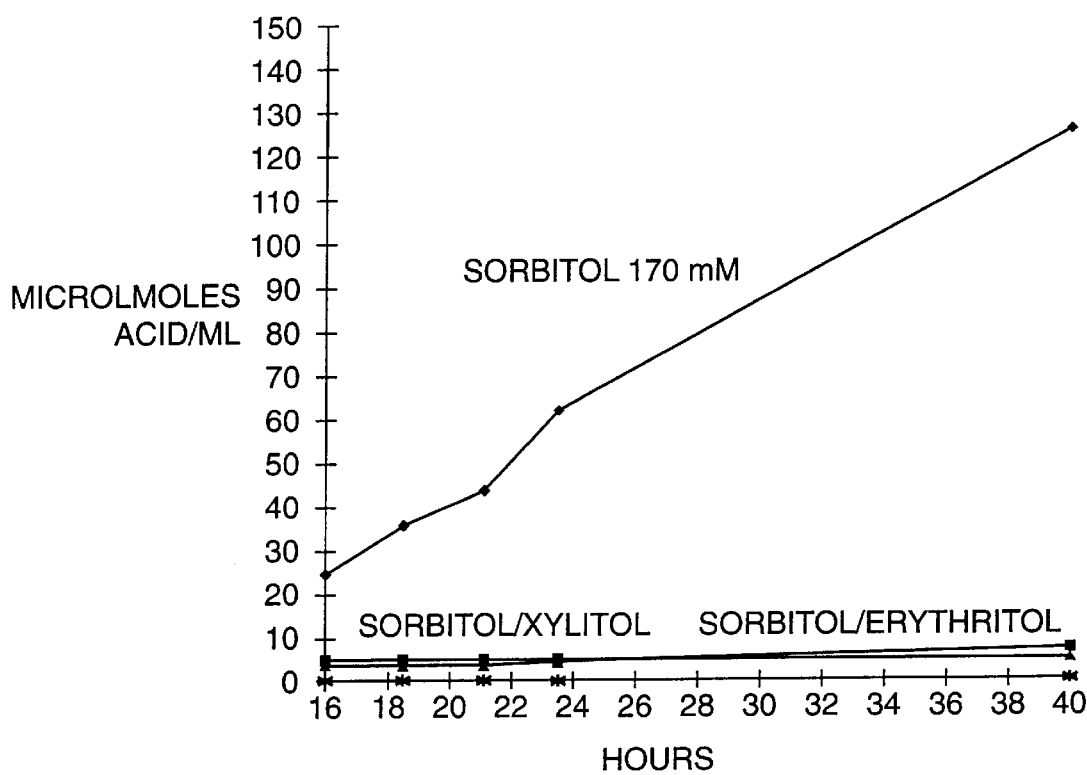
FIG. 7 shows the total amount of acid produced upon incubation of S. mutans with sorbitol, sorbitol/xylitol and sorbitol/erythritol.
Figure 8:
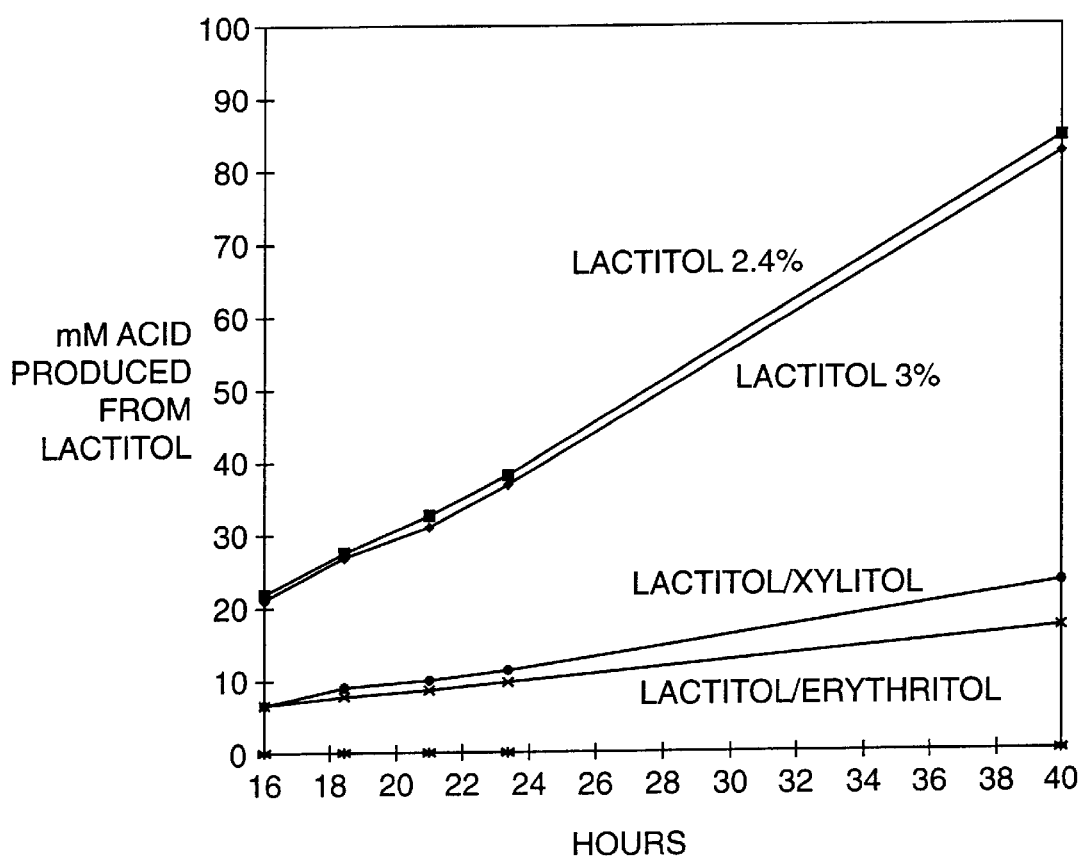
FIG. 8 shows the total amount of acid produced upon incubation of S. mutans with lactitol, lactitol/xylitol and lactitol/erythritol.

The above was confirmed when the amount of acid produced was measured (FIG. 7). Finally it was shown that the effect observed for sorbitol was also found when lactitol was used instead of sorbitol (FIG. 8).

Figure 9:
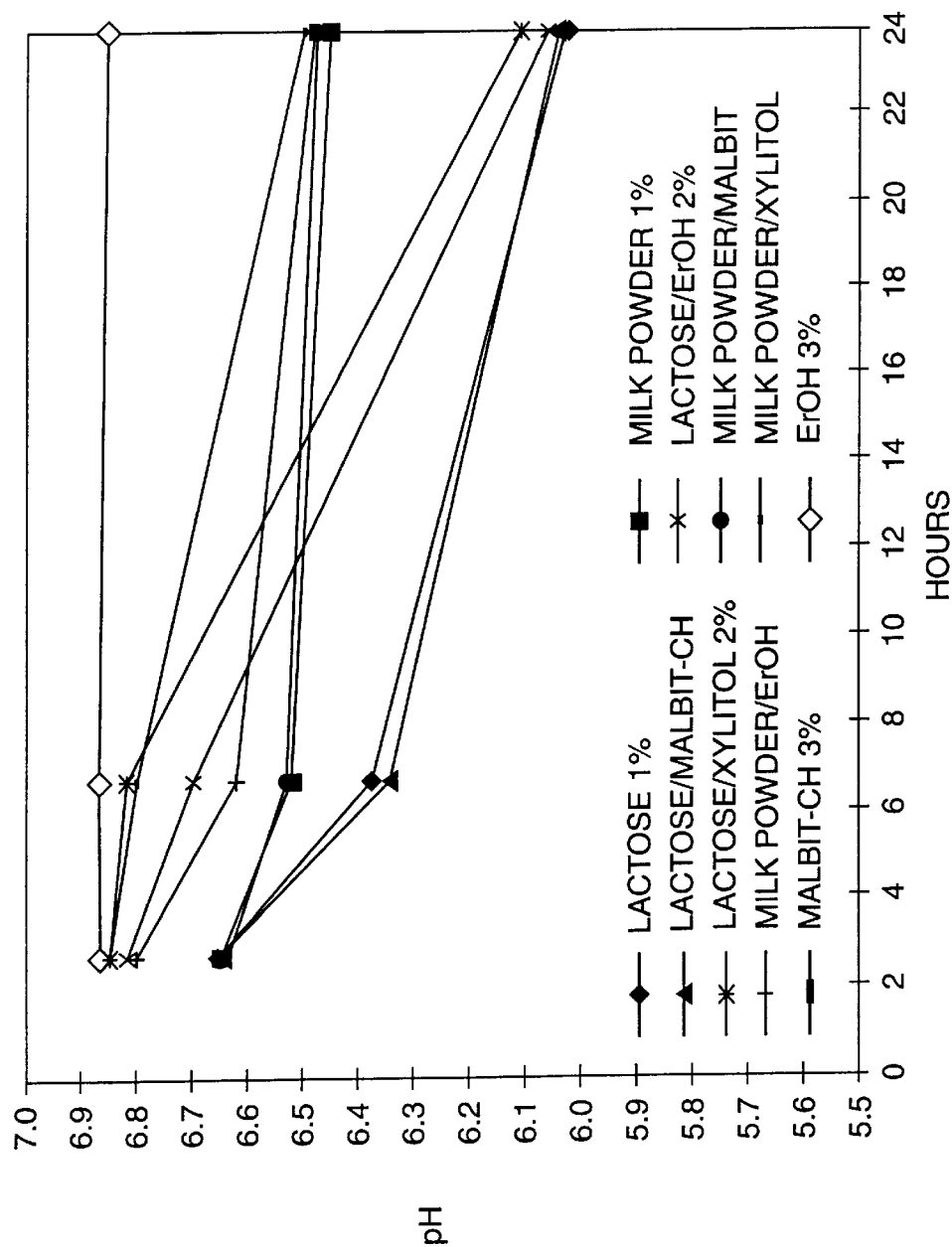
FIG. 9 shows the pH development when S. mutans is incubated with lactose or milk powder in the presence or absence of Malbit Ch, xylitol or erythritol(ErOH).
Figure 10:
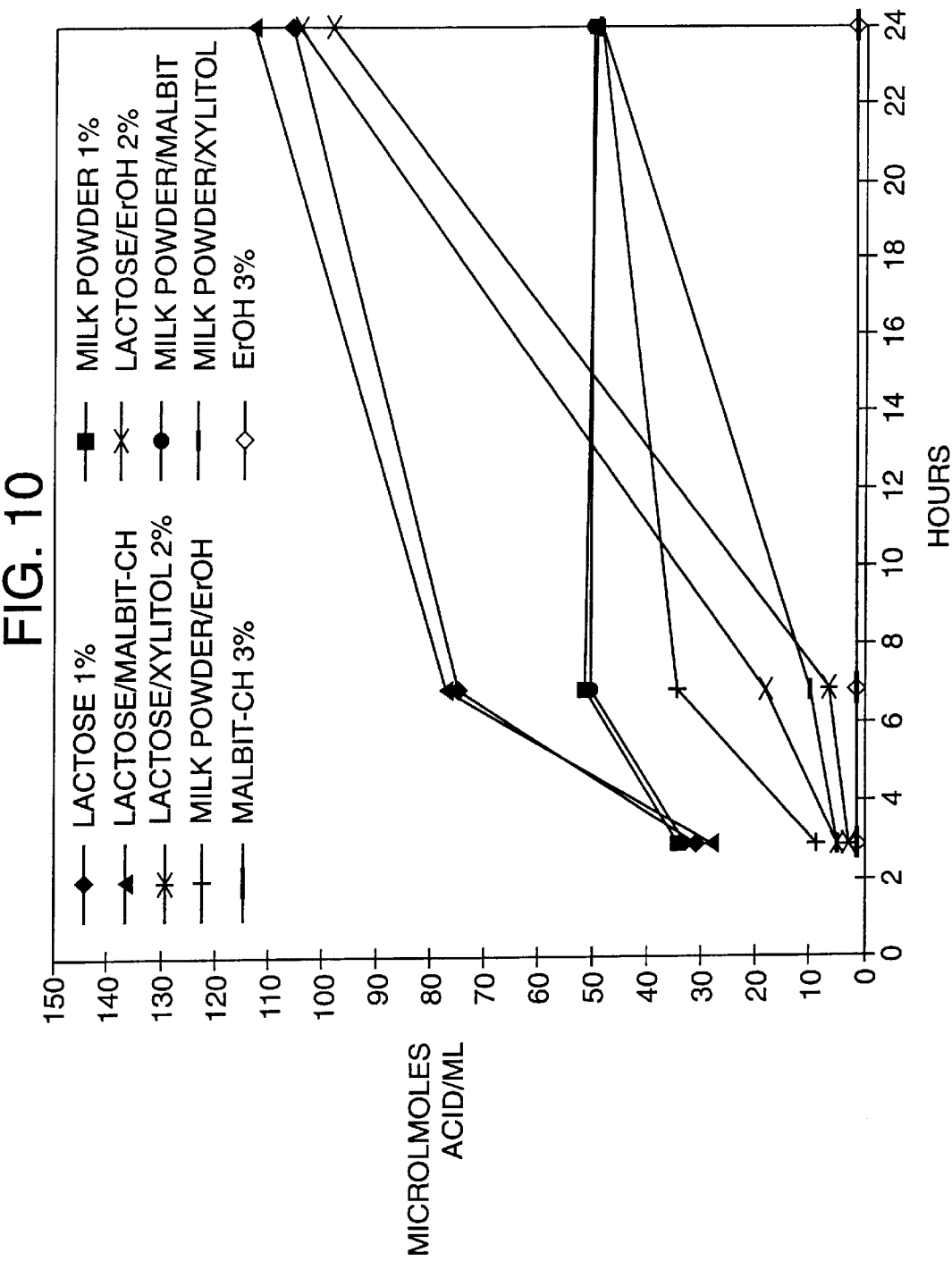
FIG. 10 shows the total amount of acid produced upon incubation of S. mutans with lactose or milk powder in the presence or absence of Malbit Ch, xylitol or erythritol (ErOH).

Example 5 describes the effect of the presence of erythritol or xylitol on the pH development by *S. mutans* when lactose and milk powder are present (FIG. 9). The effect on total acid production is also followed (FIG. 10). It appears that the pH lowering effect of lactose and milk powder is considerably lowered by the addition of erythritol.

The same effect is observed when the erythritol is incorporated in milk chocolate (FIGS. 11 and 12). The effect of lactose can therefor be counteracted by the addition of a limited amount of erythritol to sugar free milk chocolate.

These last examples disclose a sugar free non-cariogenic milk chocolate.

The sugar is replaced with erythritol in the example it can however also be replaced with a combination of erythritol and maltitol, sorbitol, lactitol or isomalt as long as there is enough erythritol present to give the anti-cariogenic effect against the lactose present in the milk powder. Milk powder can be present in amounts between 15 an 30%. The amount of erythritol should be adapted accordingly. It may also be advantageous to replace only a part of the sugar. It has been determined that to observe a certain anti-cariogenic effect or at least a lowering of the cariogenicity at least about 14% of the sugar is to be replaced with erythritol.

Finally it is also possible to combine erythritol with xylitol.

The invention discloses a non-cariogenic milk chocolate composition containing between 15 and 30% whole milk powder and between 35.5 and 50.5% sweetener wherein the sweetener selected form the group consisting of erythritol and a mixture of erythritol with sucrose, sorbitol, lactitol, maltitol, xylitol or isomalt.

It can be concluded that like xylitol, erythritol has an anti-cariogenic activity.

The practical use of this activity depends on the relative amounts of sugar and erythritol. It is clear that this phenomenon is not restricted to the use of specific substrates or specific Streptococcus strains or species.

This effect is for erythritol at least as strong as the anti-cariogenic activity of xylitol. The present invention further discloses the use of erythritol as a partial replacer of other known sweetening agents. Erythritol is used for partial replacement of sugar in different applications and the product is still considered as non-cariogenic.

EXAMPLES

Experimental

The method used in the present examples is an in-vitro cariogenicity test. In this test 'in -vitro' fermentability of carbohydrates by the mouth bacterium *Streptococcus mutans*, is investigated under defined conditions. The test is set up as follows. In a medium, consisting of a simple nitrogen source with the test substance as sole carbon source, buffered with a physiological buffer, organic acid production is recorded over time.

1. Medium Constituents carbohydrate: 0.85M stock solution. Final concentration in test volume is 170 mM.

nitrogen source: 6.7% d.s. Yeast Nitrogen Base (YNB from Difco) Final concentration in test is 0.67% d.s.

buffer: 1.25M MES (morpholino-ethane-sulfonic acid) suspension is adjusted to pH=7.2 with concentrated NH4OH (MES is solubilised during pH adjustment). Final concentration in test is 0.25M.

The solutions were sterilised by filtration (0.22$\mu$)

Each sterile 'in vitro' test tube (15×150 mm, metal stopper) contained the following ingredients (for a 5 ml test):

1.0 ml carbohydrate stock solution (0.85M)

1.0 ml MES-buffer 0.5 ml YNB-solution 1.5 ml sterile distilled water 1.0 ml inoculum A 5 ml test is generally used when low cariogenic substrates are tested, because of the high inoculum density, which is needed for these substrates; for cariogenic substrates (as sucrose, dextrose) the test is performed in 10 ml (all volumes are doubled).

2. Inoculum Preparation

A stock culture is prepared by transferring *Streptococcus mutans* -TCV264(ATCC25175) from TBAbase (Tryptose Blood Agar base) slants to TSB (Tryptic Soy Broth)-MES buffer (3% TSB-0.06M) in 1L flask, pH7.2, and grown at 37° C. for 16 hours, 100strokes/min shaking. Bacteria are concentrated by centrifugation (10 minutes at 3000 g). Cells are washed with physiological buffer (0.04% NaCl, 0.3% KH2PO4, 0.7% Na2HPO4.2H2O, +0.5% Tween 80) and centrifuged again.

The final precipitate is resuspended in a minimal volume (25 ml) of the same buffer, to contain approx. 2–5×10e10 cells/ml.

This stock culture is transferred into sterile REVCO-vials (1 ml/vial), immediately frozen in liquid nitrogen and stored at −70° C.

A vial with frozen *S. mutans* cells is used to inoculate a sterile 0.5L flask with 500 ml TSB-MES buffer, slightly agitating in a waterbath to dispers the cells. The culture is grown under the same conditions, as described above, during 5–7 hours (pH=6.3–6.4 and O.D. 660=0.8–0.9).

Cells are then harvested and resuspended in 10 ml physiological buffer (=50× concentrated). Control platings on slants with Bile Esculin Agar are performed to check the purity and concentration of this cell-suspension.

Because of practical reasons and of the difficulty of viable cell count with Streptococci, the cell density is estimated several times by incubation of the inoculum on dextrose as substrate, with three different amounts of cells, and the acid production rate is observed.

As inoculum for the test 1.0 ml of the above obtained suspension is used to inoculate the test tubes of the in vitro test.

All manipulations are carried out in a sterile environment.

3. In-vitro Test Conditions and Sampling

Inoculated test tubes are incubated, without shaking, at 37° C. Test tubes are agitated on a Vortex, just before sampling. At appropriate time intervals, sterile samples (0.8 ml) are taken, centrifuged for 5' at 3000 g and supernatant is filtered through 0.45µ filter (non-sterile). The pH is measured 0.5 ml Samples are transferred to 1 ml HPLC-vials with 0.25 ml I.S. (internal standard=butyric acid 8 mg/ml in 0.225M H2SO4). The samples are kept frozen (−20° C.), when immediate HPLC analysis is not possible.

Depending on the type of carbohydrate under investigation, different inoculum concentrations and different time intervals for sampling are chosen.

For polyols and alternative sweeteners, acid evolution is followed in a 16 to 40 hour interval, using approx. 5×10e9 cells/ml inoculum in the test tube.

For glucose, fructose, sucrose and other fermentable carbohydrates, the faster acid production, requires an interval from 1 to 24 hours and a 10 times lower inoculum density in the test tubes.

4. Analysis and Calculation of Results

Organic acids are determined by HPLC, on a Sodex KC811-column in H+form, at 65° C. and eluted with 0.01% H2SO4 at 0.8 ml/min and an injection volume of 25 µl; detection with UV at 210 nm.

Areas of lactic, formic and acetic acid peaks are recorded and corrected with butyric acid as internal standard. HPLC results are expressed in micromol acid/ml or in mM.

Example 1

Non-cariogenicity of Erythritol

FIG. 1 shows the results of the test for the (non)-cariogenicity of erythritol. *Streptococcus mutans* was incubated in the presence of erythritol and sucrose as control. The pH of the solution was measured as a function of time. Sucrose induced a sharp pH drop whereas the pH of the solution containing erythritol remained constant.

Lactic acid production was also measured as a function of time. As can be seen from FIG. 2 no lactic acid was produced from erythritol.

These results indicate that erythritol is not fermented by *Streptococcus mutans* and does not give rise to acid production. It can therefore be considered as non-cariogenic.

Fermentability of erythritol has also been tested with other strains of Streptococci, namely *Streptococcus sobrinus* and *Streptococcus rattus*. In all cases the fermentability of erythritol was almost zero. Fermentability of glucose was considerable after 24 hours as evidenced by lactic acid production in all tested cases (see FIG. 3). Different strains of *Streptoccocus mutans* were also compared to check the variability within this species. None of the strains were able to produce lactic acid starting from erythritol (see FIG. 4).

Example 2

Anti-cariogenicity of Erythritol compared with that of Xylitol

In order to study whether erythritol could have a similar effect as xylitol on the dental plaque flora, xylitol and erythritol were incubated in the presence of other polyols. Sorbitol is very slowly metabolised by lactic acid bacteria and gives rise to a very slow acidification.

Blends of 80% sorbitol (140 mM) and 20% xylitol or 20% erythritol (30 mM) were incubated in the presence of *S. mutans*. A test with 170 mM sorbitol was used as a control. The addition of xylitol inhibited almost completely the pH decrease over time indicating an inhibition of the bacteria by this polyol (see FIG. 5). Similarly erythritol tested under identical conditions showed the same effect (see FIG. 6).

Measurements of the acidity produced showed an almost complete inhibition of the production when 20% erythritol was added in the mixture (FIG. 7). Lower erythritol contents resulted also in a very strong reduction of the *S. mutans* activity. A similar effect was observed when replacing sorbitol by lactitol. Both xylitol and erythritol showed an inhibitory effect on the lactic acid bacteria (FIG. 8).

Example 3

Selected Candy Compositions Containing Erythritol a) Sugar-free Gelatine Gums

Sugar-free gelatine gums with taste, sensorial properties and texture equivalent to conventional sweetened gums are obtained using Maltidex$^r$ 110 syrup. A part of the Maltidex 110 is replaced with erythritol.

| Basic formulation (medium hardness) | | | |
|---|---|---|---|
| Gelatine | | | |
| A | 220 Bloom | 6% | 6% |
| | water | 12% | 12% |
| B | Maltidex 110 | 82% | 65.6% |
| | Erythritol | | 16.4% |
| | Citric acid 50% | as needed | |
| | Colour and flavour | as needed | |

Gelatine solution is prepared by adding the gelatine to warm water (60° C). Maltidex+erythritol solution is prepared at the desired substance of 90%. The Maltidex solution is cooled to 100° C. and mixed with the gelatine solution. The mix is cooled to 80° C. and the citric acid, colour and flavour are added. The product is cooled and stored. Taste and texture are excellent and cariogenic activity was found to be absent.

b) Sugar-free Gum Arabic Pastilles

Sugar-free gum arabic pastilles are prepared as follows with taste, sensorial properties and texture equivalent to conventional sweetened gums are obtained using Maltidex$^r$ 100 syrup. A part of the Maltidex 100 is replaced with erythritol.

| Basic formulation (soft hardness) | | |
|---|---|---|
| Gum arabic solution 50% d.s. | 44.6% | 44.6% |
| Maltidex 100 | 65.4% | 52.4% |
| Erythritol | | 13% |
| Citric acid 50% | as needed | |
| Colour and flavour | as needed | |

Matidex solution is mixed with erythritol and gum arabic solution. The mix is cooked at 70–72% d.s. at 110° C. De-aerated for 30 minutes at moulding temperature and moulded. The product is not sticky or brittle. The anti-cariogenic activity of erythritol is apparent upon consumption of these gums c) Sugar-free Chewy Candy Whereas Maltidex 100 is suitable for non-grained type candies having a longer texture Maltidex 100 combined with erythritol is suitable for having a grained type shorter texture candy. Stickiness is avoided by adding a small amount of lecithin. Gelatine solution is prepared by adding the gelatine to warm water (60° C.) Maltidex+erythritol solution is prepared at the desired substance of 90%. The Maltidex solution is cooled to 100° C. and mixed with the gelatine solution.

| Formulation | non-grained | grained |
|---|---|---|
| Maltidex 100 | 88% | 70.4% |
| Erythritol | | 17.6% |
| Gelatine sol. | | |
| Gelatine Bloom 150 | 1.5% | |
| water | 2.7% | |
| Fat | | |
| hydrogenated cacao fat (melting point 34–36° C.) | 7.0% | |
| GMS | 0.6% | |
| Lecithin | 0.2% | |

Gelatina is dissolved in warm water Maltidex is heated (with erythritol) 136–145° C. GMS and lecithin are mixed with the molten fat and added to Maltidex. Gelatine is added under mixing. The mass is cooled and the taste is pulled.

d) Other Compositions

In similar ways sugar-free fondant, sugar-free hard candies and sugar-free fudge are made. In all these compositions the erythritol partially replaced the maltitol with the expected benefit.

Example 4

Chewing Gum Composition Containing Erythritol

Low liquid phase chewing gum formulations of the composition presented in Table 1 were prepared as follows. Erythritol was used in such an amount that about 20% of the sorbitol was replaced.

The kneader is heated to about 50° C. and warm gum base having about the same temperature is added. Kneading is continued for 5 minutes. 50% of the sorbitol powder and/or the erythritol are added and kneading is continued for 5 minutes. The remaining sorbitol powder is added, kneading is continued for 5 minutes.

Glycerol is added and kneading is continued for 3 minutes. Finally, the flavour is added and kneading is continued for 5 minutes. The mass is then extruded and laminated.

TABLE 1

Low liquid phase chewing gum formulation

| | 100% sorbitol % | 20% polyol % |
|---|---|---|
| Gum base | 35 | 35 |
| Sorbitol powder (P6) | 46 | 37.2 |
| Polyol type | — | 9.2 |
| Mannitol | 15 | 15 |
| Glycerol | 2 | 2 |
| Mint flavour | 2 | 2 |

Hardness determination of the gum mass after preparation. The hardness measurement of the gum mass obtained by penetration at different temperatures shows no significant differences for the tested products. The pure sorbitol type (P6 grade) is slightly harder but the softer gum mass with the polyols has no negative influence on further processing e.g. extrusion.

The presented chewing gum composition is non-cariogenic.

Example 5

Anti-cariogenicity of Erythritol on Lactose and Milk Powder

In order to study whether erythritol has an anti-cariogenic effect on chocolate components the cariogenicity test was repeated with the following samples. Lactose 1%, milk powder 1%, malbit Ch 3%, erythritol 3% and xylitol 3%. Blends were used having the following compositions.

Lactose 1% /Malbit Ch 2%,

Lactose 1% /Erythritol 2%

Lactose 1% /Xylitol 2%

Milk powder 1% /Malbit Ch 2%

Milk powder 1% /Erythritol 2%

Milk powder 1% /Xylitol 2%

The results in the form of the pH development in time are shown in FIG. 9. From this figure it appears that after 3 to 6 hours lactose, milk powder, and lactose and milk powder blended with Malbit Ch show a considerable lowering of the pH. Clearly Malbit Ch does not positively influence the lowering of the pH.

The lowering of the pH observed in the presence of both lactose and milk powder is considerably retarded upon addition of xylitol or erythritol. Erythritol is thus having an anti-cariogenic effect. The pH lowering activity caused by lactose and milk powder is blocked to a considerable degree in the presence of erythritol.

Measurements of the acidity produced showed an almost complete inhibition of the acid production for up to three hours when erythritol or xylitol were added (FIG. 10).

Example 6

Sugar Free Milk Chocolate Containing Erythritol

Erythritol was used in sugar free milk chocolate. Cariogenicity was determined based on the pH development and the total amount of acid produced.

TABLE 2

Sugar free milk chocolate formulation

| Cocoa mass | 11.5% |
|---|---|
| Cocoa butter | 23.5% |
| erythritol | 42.5% |
| whole milk powder | 22.0% |
| lecithin | 0.5% |

The chocolate was prepared as follows. Erythritol, cocoa mass, about 7% of the cocoa butter and whole milk powder were mixed for 15 min. at 40° C. The paste was milled on a refiner to obtain a particle size of about 40 to 60 μm. After 1 hour of dry conching about 70% of the remaining cocoa butter was added. Conching was at 55–60° C. for a total of 22 hours. Two hours before the end of the conching time the remaining cocoa butter was added. One hour before the end of the conching the lecithin was added. Tempering or tabletting was performed at 30–31° C.

For comparative purposes dark chocolate was also prepared according to standard methods.

The following samples were tested.

Dextrose 3%,

Milk powder 3%,

Malbit Ch 3%,

Malbit Ch as sugar replacer in milk chocolate,

Malbit Ch as sugar replacer in dark chocolate,

Milk powder 1% /Erythritol 2%,

Erythritol as sugar replacer in milk chocolate, (samples in the form of ovals or squares)

Erythritol as sugar replacer in dark chocolate.

The results in the form of the pH development in time are shown in FIG. 11. From this figure it appears that after 3 to 6 hours the pH lowering activity ascribed to the presence of lactose in milk chocolate lactose is considerably reduced by the addition of erythritol.

In dark chocolate there is of course no effect from the milk powder (lactose) therefore in this case the non-cariogenic effect is actually measured.

Measurements of the total acidity produced showed an almost complete inhibition of the acid production for up to three hours when erythritol was added to milk chocolate until up to 3 hours (FIG. 12).

What is claimed is:

1. A method of preparing a non-cariogenic composition containing a sugar or a cariogenic sweetening agent and erythritol comprising:
   replacing a portion of said sugar or cariogenic sweetening agent in an orally administered cariogenic composition with from 5 to 19.8% erythritol.

2. A method according to claim 1, further comprising replacing in an orally administered composition containing at least one of sucrose, sorbitol, lacititol, maltitol or isomalt with from 5 to 19.8% erythritol.

3. A method according to claim 1, wherein said sweetening agent is a cariogenic polyol.

4. A method according to claim 3, wherein said polyol comprises at least one of sorbitol or lactitol.

5. A method according to claim 1, wherein up to 14% of said sugar is replaced by erythritol.

* * * * *